(12) United States Patent
Möbius et al.

(10) Patent No.: US 11,535,822 B2
(45) Date of Patent: Dec. 27, 2022

(54) DEVICE FOR ISOLATING STEM CELLS FROM FETAL TISSUES

(71) Applicant: MDTB CELL MANUFACTURING GMBH, Dresden (DE)

(72) Inventors: Marius Alexander Möbius, Dresden (DE); Mario Rüdiger, Dresden (DE); Daniel Freund, Dresden (DE)

(73) Assignee: MDTB CELL MANUFACTURING GMBH, Dresden (DE)

( * ) Notice: Subject to any disclaimer, the term of this patent is extended or adjusted under 35 U.S.C. 154(b) by 249 days.

(21) Appl. No.: 16/321,553

(22) PCT Filed: Jul. 28, 2017

(86) PCT No.: PCT/EP2017/069192
§ 371 (c)(1),
(2) Date: Jan. 29, 2019

(87) PCT Pub. No.: WO2018/020008
PCT Pub. Date: Feb. 1, 2018

(65) Prior Publication Data
US 2019/0185809 A1   Jun. 20, 2019

(30) Foreign Application Priority Data

Jul. 29, 2016   (DE) ..................... 10 2016 114 043.0

(51) Int. Cl.
*C12M 1/33* (2006.01)
*C12M 1/00* (2006.01)
(Continued)

(52) U.S. Cl.
CPC ............ *C12M 45/02* (2013.01); *C12M 45/09* (2013.01); *C12N 5/0605* (2013.01); *C12N 5/0668* (2013.01)

(58) Field of Classification Search
None
See application file for complete search history.

(56) References Cited

U.S. PATENT DOCUMENTS 4,028,190 A * 6/1977 McAleer ................... B04B 1/04
435/289.1
4,797,213 A * 1/1989 Parisius ................. C12M 45/02
210/651
(Continued)

FOREIGN PATENT DOCUMENTS

CN         202519256 U *  11/2012 ............ C12M 23/08
EP         2 433 713 A2     3/2012
(Continued)

OTHER PUBLICATIONS

Han et al., Optimization of human umbilical cord mesenchymal stem cell isolation and culture methods, 2013, Cytotechnology, 65: 819-827 (Year: 2013).*

(Continued)

*Primary Examiner* — Holly Kipouros
(74) *Attorney, Agent, or Firm* — Maschoff Brennan

(57) ABSTRACT

The invention relates to a device for isolating stem cells from fetal tissues, which device has an incubation chamber, at least one pump, at least one reservoir for a tissue breakdown solution, at least one reservoir for a rinsing solution, optionally a control unit, optionally a means for removing contaminants, and optionally a means for expansion of the isolated stem cells. The invention further relates to a method for isolating stem cells from fetal tissue, which method comprises, among other things, the mechanical dissociation and the enzymatic digestion of the fetal tissue and optionally density gradient centrifugation for removing contaminants. The device and the method according to the invention are particularly suitable for isolating mesenchymal stem cells (Continued)

Figure 1:
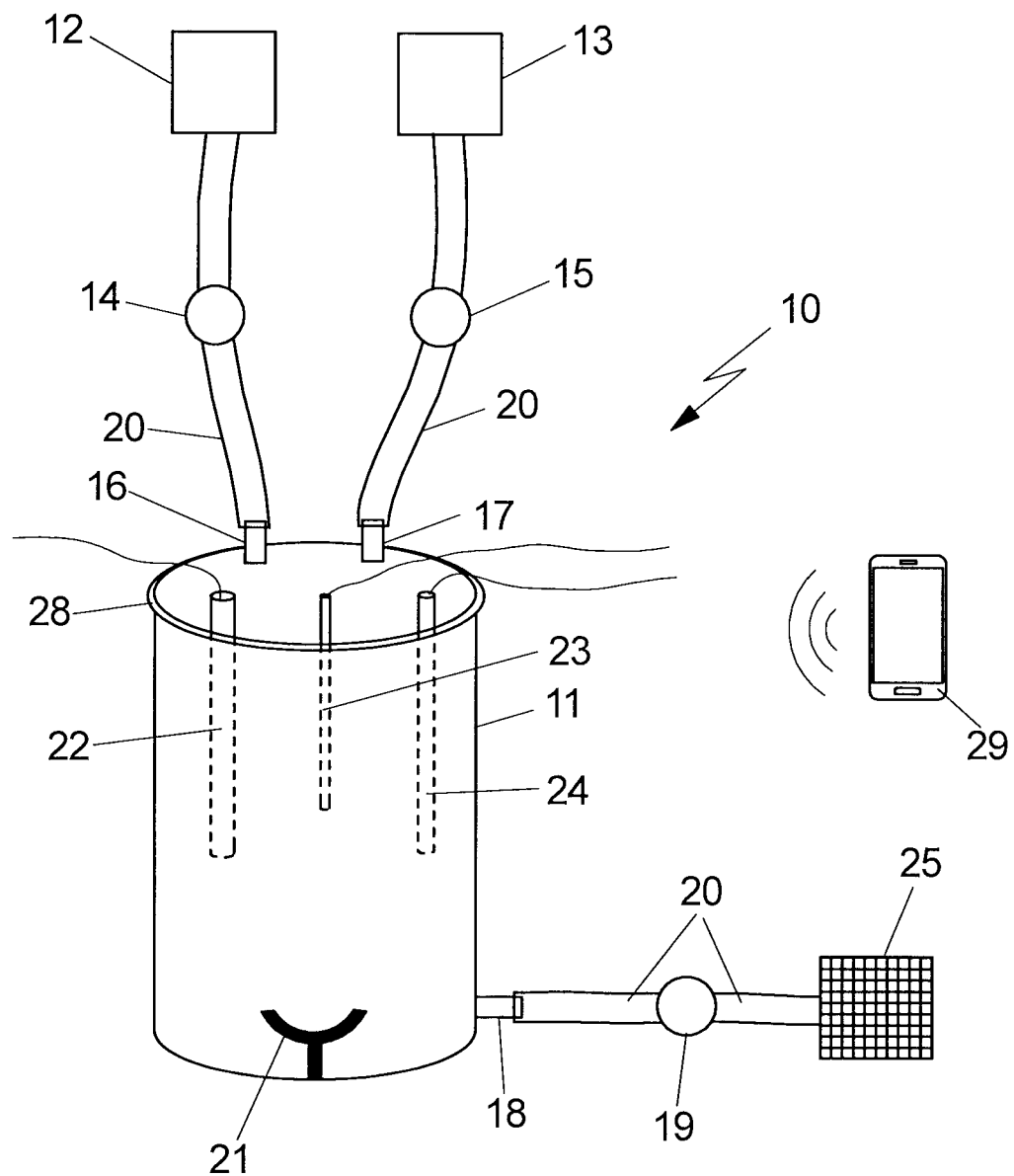

from fetal tissues, such as umbilical cord tissue, placenta tissue, or fetal lung tissue.

18 Claims, 3 Drawing Sheets

(51) Int. Cl.
*C12N 5/073* (2010.01)
*C12N 5/0775* (2010.01)
*C12M 1/42* (2006.01)
*C12M 1/02* (2006.01)
*C12M 3/08* (2006.01)

(56) References Cited

U.S. PATENT DOCUMENTS

| | | | |
|---|---|---|---|
| 6,911,201 B1* | 6/2005 | Merchav | C12N 11/08 |
| | | | 424/93.7 |
| 9,273,275 B2 | 1/2016 | Kobayashi et al. | |
| 2003/0161816 A1* | 8/2003 | Fraser | A61P 27/02 |
| | | | 424/93.7 |
| 2005/0260175 A1 | 11/2005 | Hedrick et al. | |
| 2011/0008397 A1* | 1/2011 | Cohen | A61L 27/3604 |
| | | | 424/400 |
| 2011/0281319 A1* | 11/2011 | Swayze | C12M 47/04 |
| | | | 435/173.9 |
| 2013/0028813 A1* | 1/2013 | Shioyama | C12M 45/02 |
| | | | 422/534 |
| 2013/0295673 A1* | 11/2013 | Taghizadeh | B02C 18/10 |
| | | | 435/379 |
| 2017/0226466 A1* | 8/2017 | Grillo | B09B 3/00 |

FOREIGN PATENT DOCUMENTS

| | | |
|---|---|---|
| JP | 2011-097878 A | 5/2011 |
| JP | 2011-172545 A | 9/2011 |
| WO | 2005035742 A2 | 4/2005 |
| WO | 2006094286 A2 | 9/2006 |
| WO | 2009006422 A1 | 1/2009 |
| WO | 2010130302 A1 | 11/2010 |
| WO | 2015170347 A2 | 11/2015 |

OTHER PUBLICATIONS

Document entitled Description CN202519256U, English machine translation of CN202519256U provided by Espacenet, 2012 (Year: 2012).*

Moshiri et al., Comprehensive Imaging Review of Abnormalities of the Umbilical Cord, 2014, Radiographics, 34:179-196 (Year: 2014).*
T.R.J. Heathman et al., "The translation of cell-based therapies: clinical landscape and manufacturing challenges ", Regen Med, vol. 10, No. 1, pp. 49-64, 2015.
M. Mendicino et al., "MSC-based product characterization for clinical trials: an FDA perspective.", Cell Stem Cell, vol. 14, No. 2, pp. 141-145, Feb. 2014.
P. Wuchter et al., "Standardization of good manufacturing practice-compliant production of bone marrow-derived human mesenchymal stromal cells for immunotherapeutic applications.", Cytotherapy, vol. 17, No. 2, pp. 128-139, Feb. 2015.
R. Hass et al., "Different populations and sources of human mesenchymal stem cells (MSC): A comparison of adult and neonatal tissue-derived MSC.", Cell Commun Signal, vol. 9, p. 12, May 2011.
I. Majore et al., "Growth and differentiation properties of mesenchymal sliomal cell populations derived from whole human umbilical cord.", Stem Cell Rev, vol. 7, No. 1, pp. 17-31, Mar. 2011.
R. Sarugaser et al., "Human umbilical cord perivascular (HUCPV) cells: a source of mesenchymal progenitors.", Stem Cells, vol. 23, No. 2, pp. 202-229, Feb. 2005.
N. Tsagias et al., "Isolation of mesenchymal stem cells using the total length of umbilical cord for transplantation purposes.", Transfus Med, vol. 21, No. 4, pp. 253-261, Aug. 2011.
M.M. Lalu et al., "Safety of cell therapy with mesenchymal stromal cells (SafeCell): a systematic review and meta-analysis of clinical trials.", PLoS One, vol. 7, No. 10, pp. e47559, Oct. 2012.
P. Monsarrat et al., "An Innovative, Comprehensive Mapping and Multiscale Analysis of Registered Trials for Stem Cell-Based Regenerative Medicine.", Stem Cells Transl Med, vol. 5, No. 6, pp. 826-835, Jun. 2016.
T. van Haaften et al., "Airway delivery of mesenchymal stem cells prevents arrested alveolar growth in neonatal lung injury in rats.", Am J Respir Crit Care Med, vol. 180, No. 11, pp. 1131-1142, Dec. 2009.
Y.S. Chang et al., "Mesenchymal stem cells for bronchopulmonary dysplasia: phase 1 dose-escalation clinical trial.", J Pediatr, vol. 164, No. 5, pp. 966-972, May 2014.
M.A. Möbius, B. Thébaud, "Cell Therapy for Bronchopulmonary Dysplasia: Promises and Perils.", Paediatr. Respir. Rev. in press (2016).
G. Yannarelli et al., "Human umbilical cord perivascular cells exhibit enhanced cardiomyocyte reprogramming and cardiac function after experimental acute myocardial infarction.", Cell Transplant, vol. 22, No. 9, pp. 1651-1666, 2013.
EP Office Action in Application No. 17 749 164.4 dated Nov. 11, 2019.

* cited by examiner

DEVICE FOR ISOLATING STEM CELLS FROM FETAL TISSUES

FIELD OF THE INVENTION

The invention relates to a device for isolating stem cells from fetal tissues that comprises an incubation chamber, at least one pump, a reservoir for a tissue-disruption solution, a reservoir for a rinse solution, optionally a control unit, optionally a means for the removal of impurities and optionally a means for the expansion of the isolated stem cells. The invention further relates to a method for isolating stem cells from fetal tissue that comprises, inter alia, the mechanical dissociation and the enzymatic digestion of the fetal tissue and optionally a density-gradient centrifugation for the removal of impurities. The device and the method of the invention are particularly suited to isolating mesenchymal stem cells from fetal tissues, such as umbilical cord tissue, placenta tissue or fetal lung tissue.

BACKGROUND OF THE INVENTION

Owing to their immunomodulatory and tissue-regeneration-promoting properties, stem cells, especially mesenchymal stromal cells (MSCs), are successfully tested in many preclinical and clinical studies (Heathman et al., 2015). However, the vast majority of the cells used originates from the bone marrow (so-called bone marrow MCSs or BM-MSCs). They are qualitatively inhomogeneous owing to the donor's age, the low amount of usable bone marrow and the resultant need for a dramatic cell expansion (Mendicino et al., 2014; Wuchter et al., 2015) and thus suitable only to a very limited extent for broad application in the context of regenerative therapy approaches. To obtain BM-MSCs, it is also necessary to perform an invasive procedure (bone marrow puncture), which encompasses a small operation with local anesthesia and sedation. By contrast, the umbilical cord is a waste product, from which fetal stem cells can be obtained without these risks for the donor.

MSCs are mesenchymal progenitor cells which occur in virtually all mesodermal tissues and the umbilical cord/the placenta. MSCs are potently anti-inflammatory and stimulate the growth and the regeneration of various tissue (vessels, lung, etc.). They can therefore be used for the treatment of diseases involving an excessive inflammatory reaction, impaired vascularization and/or consequent tissue damage. Worldwide, well over 1000 patients have so far been treated with autologous or allogenic MSCs from various tissues (Lalu et al., 2012); almost 1000 clinical studies have already been completed or are being carried out (Monsarrat et al., 2016). MSCs can, for example, be used as cell therapeutics in the case of dysfunction or hypofunction of the premature lung (van Haaften 2009, Chang 2014). The administration of exogenous MSCs led to the interaction with the lung tissue and to the "needs-based" secretion of proteins, small molecules and cellular components (e.g., exosomes, mitochondria). The result is protection of the endogenous lung cells as well as stimulation of lung growth (Möbius 2016).

However, the use of MSCs as pharmaceutical product presents itself as problematic. None of the MSC populations used to date in clinical studies corresponded, in terms of their production, to a classic pharmaceutical product. Each cell product, each lot or each batch is different and the results of the clinical studies are not comparable. The same applies to conventionally produced cell-free products, for example conditioned, purified cell-culture medium; exosomes, etc.

Moreover, MSCs are an inhomogeneous cell population. The MSCs obtained from a donor differentiate in culture owing to various factors, some into therapeutically inactive cells, some into transdifferentiated cells and some into therapeutically active cells. The harvested and hitherto used cell product is a variable mixture composed of therapeutically active, less active or nonactive cells.

Umbilical cord MSCs are an alternative to the MSCs from "classic" sources such as bone marrow (BM-MSCs) and adipose tissue (AT-MSCs). These classically obtained MSCs have various disadvantages. For instance, BM-MSCs are often highly expanded cells from relatively old donors. The proportion of therapeutically active cells both in the starting material and in the end product is low. The isolation of MSCs from bone marrow and adipose tissue is always associated with an invasive procedure (puncture).

By contrast, MSCs from umbilical cord have advantages. The umbilical cord is a de facto infinite source of "young" MSCs. In the case of the treatment of myocardial infarctions, MSCs from the umbilical cord are therapeutically superior to the BM-MSCs (Yannarelli et al., 2013).

Approaches for isolating MSCs from hitherto discarded tissues (including umbilical cord tissue) exist (Hass et al., 2011), but have problems which prevent the broad application of said MSCs. Methods to date involve either the gradual migration or the outward growth of MSCs from umbilical cord tissue cut into small pieces (Majore et al., 2011) or the enzymatic dissociation of the mechanically pretreated tissue (Sarugaser et al., 2005; Tsagias et al., 2011).

None of the conventionally used methods provides a sufficiently large number of qualitatively high-value MSCs for clinical applications, since the population doubling number of the individual cells is excessively high and/or the digestion and the subsequent further processing of the cell product is not compatible with a closed environment which meets the standard of good manufacturing practice (GMP).

WO 2006/094286 provides a method for isolating stromal cells from pancreas tissue. The method comprises both the mechanical dissociation and an enzyme digestion of the pancreas donor tissue. The isolated stromal cells from the pancreas can be induced in vitro for differentiation into complete or partially differentiated pancreas cells for transplantation in a patient. Alternatively, the isolated pancreas stromal cells can be directly transplanted into a patient and can differentiate in vivo into the desired cell types.

EP 2 433 713 provides a system for the processing and separation of samples, comprising a sample-processing unit and a sample-separation unit. In the system disclosed in EP 2 433 713, the separation of the samples is done by means of magnetic separation. To this end, biological materials, such as, for example, cells from various organs and tissues, must be magnetically labeled with a suitable specific binding ligand.

WO 2015/170347 discloses a method for the separation, enrichment and coculture of a mixture of fetal cells that contains one or more different types of mesenchymal stem cells obtained from placenta, amnion, amniotic fluid, chorion and umbilical cord and/or other products of conception under hypoxic or normoxic conditions and that is suitable for the treatment of a multiplicity of diseases ranging from congenital diseases through to degenerative diseases and right up to malignant diseases.

The devices and methods known from the prior art are, however, burdened with the disadvantage that qualitatively high-value MSCs cannot be provided in sufficient number for clinical applications and that the batches of MSCs that are produced do not meet the requirements for good manufacturing practice (GMP).

DESCRIPTION OF THE INVENTION

It is therefore an object of the invention to provide a device which allows the GMP-compliant production of qualitatively high-value, therapeutically usable stem cells, especially MSCs, from fetal tissues for, in particular, regenerative and immunomodulatory applications in adult medicine and child medicine. Further possible applications of the isolated MSCs are veterinary medicine, drug development (MSCs as in vitro test system for pediatric or adult medicaments), research in general, etc. It is intended that the device according to the invention be, in particular, suited to providing the MSCs from fetal tissues in a GMP-compliant manner and in large amounts.

Fetal tissue in the context of the present invention is tissue which has arisen from the fertilized egg cell and the resultant embryoblasts plus trophoblasts, and is thus distinguished from the maternal tissue. Fetal tissue is preferably tissue which was immediately obtained after birth (i) of a fetus which died in the womb (stillbirth), (ii) fetus born before reaching extrauterine viability (abortion) or (iii) tissue which is removed from the newborn immediately after birth (especially the fetal membranes, the placenta and the umbilical cord).

The object of the invention is achieved by providing a device having the features as claimed in claim 1.

The device according to the invention for isolating stem cells from fetal tissues comprises in particular
an incubation chamber,
at least one pump,
at least one reservoir for a tissue-disruption solution,
at least one reservoir for a rinse solution,
optionally a control unit,
optionally a means for the removal of impurities, for example in a density gradient, and
optionally a means for the expansion of the isolated stem cells.

Compared to devices which are conventionally used, the device according to the invention has the advantage that the isolation of stem cells, especially MSCs, results in a distinctly higher yield of stem cells, especially primary MSCs. The device is particularly advantageous for the isolation of primary MSCs from the umbilical cord. Using the device according to the invention, it is possible to achieve yields which are increased by a factor of >10 with respect to devices which are conventionally used. As a result, it is possible to generate, in a shorter expansion phase, a cheaper cell product which is of higher value both quantitatively and qualitatively.

The incubation tank preferably consists of a material which is sterilizable, more particularly autoclavable. Suitable materials, for example, glass, stainless steel or autoclavable plastics.

In one embodiment of the invention, the incubation chamber is a heatable tank. This has the advantage that the disruption of the fetal tissue, which can be done enzymatically, can be carried out at temperatures optimal for the enzymes used. The temperature in the incubation chamber is, for example, adjusted to a range from 30° C. to 42° C., preferably to a range between 35° C. and 40° C. It is especially preferred when the temperature in the incubation chamber is adjusted to a temperature of 37° C. Said temperature is the optimal temperature for enzymes in the tissue-disruption solution that are of human origin.

The temperature in the incubation chamber can be regulated by means of a thermostat, a temperature probe or temperature sensor which, for example, is connected to the control unit.

The temperature of the contents of the incubation chamber can also be adjusted externally with the aid of an electric heating plate. A double-walled design of the incubation chamber 11 is conceivable, meaning that the contents of the incubation chamber can be heated by means of a liquid medium, such as water for example, and a thermostat. It is particularly preferred when the temperature in the incubation chamber is regulable by means of a Peltier element provided with a sterilizable or disposable shell.

In another embodiment, the incubation chamber can also be a nonheatable tank.

In a further embodiment, the incubation chamber can contain a pH probe. Preferably, the pH probe is connected to the control unit, meaning that signals from the pH probe can be processed in the control unit and, as a result, time and amount of addition of the rinse solution into the incubation chamber can be controlled. In addition, said embodiment also allows the control of the addition of further solutions, such as, for instance, the addition of a wash solution and/or further enzyme solutions at one or more certain times.

The incubation chamber is preferably configured such that it is possible to generate, in the incubation chamber, an atmosphere in which the oxygen content is depleted. In this connection, the oxygen content in the atmosphere of the incubation chamber is adjusted to a proportion within the range of 2-21%, preferably 2-15% or 2-10%, particularly preferably of 2-5%. To this end, the incubation chamber can comprise further ports which make it possible to carry out a gas exchange of the atmosphere of the incubation tank.

In a further embodiment, the incubation chamber contains a means for the comminution of the fetal tissue. The comminution means is used to mechanically disrupt or to dissociate the fetal tissue from which the stem cells, preferably MSCs, are to be isolated. This results in a surface enlargement of the fetal tissue, and this, in turn, facilitates a subsequent enzymatic disruption of the fetal tissue, since the access of the enzymes used to the tissue to be disrupted is improved.

In a preferred embodiment, the means for the comminution of the fetal tissue is a mechanical means, for example a cutter. In a particularly preferred embodiment, the means for the comminution of the fetal tissue is a rotating knife system. Using the comminution means present in the incubation chamber, it is possible to carry out the mechanical comminution of the fetal tissue in an automated manner. Advantages of this configuration are an increase in the yield of the stem cells to be isolated, especially primary MSCs, as well as the avoidance or minimization of contamination. A further advantage of this configuration is that the reproducibility of the isolation of stem cells, especially of primary MSCs, from fetal tissues can be improved. The automated mechanical comminution also improves the GMP-compliance of the device according to the invention and of a method for isolating stem cells that is carried out using the device according to the invention.

In a further embodiment, the incubation chamber contains a means for the mixing of the tissue-disruption suspension, preferably a means for the stirring of the tissue-disruption suspension, especially preferably a stirrer or rotor. In a particularly preferred embodiment, the mixing of the tissue-disruption suspension is achieved using the rotating knife system used for the mechanical dissociation of the tissue. In a very particularly preferred embodiment, the tissue-disruption suspension is continuously stirred in the incubation chamber with the aid of the rotating knife system. As a result, what can be achieved is that the substrate accessibility of the enzymes used for the tissue disruption is ensured at all times.

In a further embodiment, the incubation chamber comprises openings/ports for lines and hoses. Preferably, the incubation chamber comprises at least two openings for ports and lines. The incubation chamber can also comprise yet further, i.e., more than two, openings/ports for lines and hoses.

In one embodiment of the invention, a tissue-disruption solution and/or a rinse solution can be added to the incubation chamber via the openings/ports.

The tissue-disruption solution preferably contains an enzyme mixture, preferably a mixture of enzymes, particularly preferably enzymes of eukaryotic origin, especially preferably enzymes which are free from potential contamination by animal products (so-called animal origin-free (AoF) enzymes or products). Such AoF enzymes can, for example, be obtained industrially as chromatographically purified fermentation product from, for example, genetically modified microorganisms. Very particular preference is given to recombinant enzymes of human origin.

Preferably, the enzymatic digestion is carried out using an enzyme mixture, wherein the composition of the enzyme mixture is specifically adapted to the extracellular matrix composition of the fetal tissue. It is particularly preferred when the composition of the enzyme mixture is specifically adapted to the extracellular matrix composition of umbilical cord tissue.

It is especially preferred when the tissue-disruption solution contains a mixture of the enzymes hyaluronidase and/or neutral protease and/or collagenase and/or DNAse.

It is very particularly preferred when the tissue-disruption solution comprises an enzyme mixture composed of collagenase, hyaluronidase and a DNAse. It is likewise very particularly preferred when the tissue-disruption solution contains an enzyme mixture composed of collagenase, neutral protease and a DNAse.

The DNAse used in the tissue-disruption solution is preferably DNAse I, for example Pulmozyme (Roche Diagnostics). The DNAse used in the tissue-disruption solution serves for the lowering of viscosity, and this leads to an optimal separation of target cells (e.g., primary MSCs) and impurities in a subsequent density-gradient separation. It is particularly preferred when enzymes which are free from animal impurities are used in the tissue-disruption solution.

The collagenase used in the tissue-disruption solution is, for example, collagenase NB IV/VI (SERVA Electrophoresis).

Further constituents of the tissue-disruption solution are chemically defined buffer solutions or chemically defined culture media, such as, for example, Dulbecco's phosphate buffered saline (PBS) or Dulbecco's modified Eagle medium (DMEM). They can be additionally admixed with specific salts and chemically defined substances (cofactors or cosubstrates) in order to provide, in their composition, optimal support for the enzymatic digestion and to minimize the enzyme amount to be used. Furthermore, substrates for the aerobic or anaerobic metabolism of the cells should be present, preferably glucose or sodium pyruvate. The buffer solution should preferably contain a $CO_2$-independent buffer system (e.g., HEPES or sodium biphosphate).

In an alternative embodiment, it would also be possible to use normal, already GMP-compliant ($CO_2$-buffered) media, such as DMEM. In said alternative embodiment, the monitoring of the $CO_2$ concentration in the incubation chamber in addition to the monitoring of the $O_2$ concentration is, however, necessary.

The rinse solution serves for the neutralization or the rebuffering and for the lowering of viscosity of the cell suspension after mechanical comminution and after the enzymatic tissue digestion. The rinse solution is preferably a chemically defined buffer solution or a chemically defined culture medium, such as, for example, Dulbecco's phosphate buffered saline (PBS) or Dulbecco's modified Eagle medium (DMEM).

In a further embodiment, the incubation chamber comprises at least one outlet. The incubation chamber can also comprise multiple outlets. The at least one outlet serves to transfer the tissue-disruption suspension obtained after the mechanical dissociation and the enzymatic digestion into other tanks or other components of the device according to the invention.

Such a further component of the device according to the invention can, for example, be a means for the removal of impurities in a density gradient.

In a preferred embodiment, the invention therefore provides a device for isolating stem cells from fetal tissues, wherein the device comprises
    an incubation chamber,
    at least one pump,
    a reservoir for a tissue-disruption solution,
    a reservoir for a rinse solution,
    optionally a control unit,
    a means for the removal of impurities in a density gradient, and
    optionally a means for the expansion of the isolated stem cells.

The means for the removal of impurities in a density gradient can, for example, be a centrifuge. Suitable for this purpose is any conventional type of centrifuges which are suited to carrying out a density-gradient centrifugation. Preferably, the density-gradient centrifugation is carried out using a sucrose-epichlorohydrin copolymer, which is, for example, available under the brand name Ficoll®, Histopaque® or Polysucrose®. This configuration of the device according to the invention has the advantage that a highly homogeneous starting population of stem cells, especially primary MSCs, can be provided for the later expansion, since impurities, such as endothelial cells, epithelial cells and blood cells, are removed in the density-gradient centrifugation.

In another preferred embodiment, the device according to the invention comprises no means for the removal of impurities in a density gradient.

In a further embodiment, the device according to the invention comprises a means for the expansion of the isolated stem cells, especially of primary MSCs.

Said embodiment of the invention therefore provides a device for isolating stem cells from fetal tissues, wherein the device comprises
    an incubation chamber,
    at least one pump,
    at least one reservoir for a tissue-disruption solution,
    at least one reservoir for a rinse solution,
    optionally a control unit,
    optionally a means for the removal of impurities in a density gradient, and
    a means for the expansion of the isolated stem cells.

The means for the expansion of the stem cells, especially primary MSCs, can, for example, be an adherence-enrichment means. Such an adherence-enrichment means typically provides a culture surface for the isolated cells, on which surface the isolated cells can outwardly grow and proliferate. Preferably, said culture surface is a plastics surface. An adherence-enrichment means is, for example, the HYPERStack® system (Corning). Alternatively, the adherence enrichment of the isolated cells can take place in a bioreactor, with the bioreactor containing beads and the culture surface for the isolated cells being provided by the beads. Preferably, the adherence enrichment of the isolated cells is carried out in selective media for stem cells, especially primary MSCs. It is particularly preferred when the expansion of the isolated stem cells, especially primary MSCs, is carried out in a culture medium containing additives which specifically support the growth of stem cells, especially of the primary MSCs. The culture medium for the expansion of the isolated stem cells is also preferably chemically defined, free from potential contamination by animal products (AoF) and GMP-compliant. Such additives can, for example, be human platelet-rich plasma or human platelet lysate.

The means for the adherence enrichment of the isolated stem cells, especially the isolated primary MSCs, is preferably connected to the outlet of the incubation chamber for the tissue disruption by means of a hose. Preferably, the HYPERStack® system is thus connected to the incubation tank via a hose. By means of this configuration, it is possible to ensure that the disruption of fetal tissues right up to the expansion of the isolated cells can take place in a closed system.

In a particularly preferred embodiment of the invention, the reservoir for the tissue-disruption solution and/or the reservoir for the rinse solutions are also connectable to the incubation tank by means of hoses via openings/ports.

The at least one pump present in the device according to the invention, preferably two, three or more pumps depending on the requirements of the device according to the invention, can be any kind of conventionally available pumps. However, it is particularly preferred when the pumps present in the device according to the invention are peristaltic pumps. It is thus particularly preferred when the tissue-disruption solution from the corresponding reservoir and/or the rinse solution from the corresponding reservoir can be filled into the incubation tank by means of, in each case, a separate peristaltic pump. It is similarly preferred when, after performance of mechanical comminution and enzymatic digestion, the tissue-disruption suspension can be transferred by means of a peristaltic pump into either the downstream means for the removal of impurities in the density gradient, for example a density-gradient centrifuge, and/or into the following adherence-enrichment means, for example a HYPERStack® vessel or a bead-based bioreactor. This configuration has the advantage that the pumps present in the device according to the invention have no direct contact with the liquids present in the device according to the invention. This ensures that the device according to the invention is a completely closed system for isolating stem cells, especially primary MSCs.

The density-gradient centrifuge can, for example, operate according to the principle of a peeler centrifuge or can be a continuously running centrifuge (e.g., a modified, slow-running CEPA centrifuge, Carl Padberg Zentrifugenbau GmbH).

In a particularly preferred embodiment, the device according to the invention is thus a closed system.

In a further embodiment of the invention, the device is disinfectable or sterilizable, for example autoclavable, as a closed system.

In an alternative embodiment, the device is entirely or partly configured as a presterilized disposable system for one-time use. In particular, the hoses and reservoirs, possibly also the incubation chamber, and the HYPERStack® system are suited to being configured as a presterilized disposable system.

In a particularly preferred embodiment, the device according to the invention is characterized in that it contains no means for the magnetic separation of target cells (stem cells, especially MSCs) and impurities, such as, for example, endothelial cells, blood cells or epithelial cells.

In a very particularly preferred embodiment, the device according to the invention for isolating stem cells from fetal tissues is a closed system comprising
    an incubation chamber,
    a reservoir for a tissue-disruption solution,
    a pump, especially a peristaltic pump, for the transfer of the tissue-disruption solution into the incubation chamber,
    a reservoir for a rinse solution,
    a pump, especially a peristaltic pump, for the transfer of the rinse solution into the incubation chamber,
    a means for the removal of impurities in a density gradient, preferably a density-gradient centrifuge,
    and/or a means for the expansion of the isolated stem cells,
wherein said device realized as a closed system is sterilizable, preferably autoclavable, or, alternatively, is partly configured as a presterilized disposable system for one-time use.

In said embodiment, the reservoir for the tissue-disruption solution, the reservoir for the rinse solution and the means for the removal of impurities in the density gradient and/or the means for the expansion of the isolated stem cells are connected to the incubation chamber via autoclavable hoses or, preferably, via disposable hoses.

This configuration as a closed system has numerous advantages. Cell harvesting and cell yield is distinctly improved in comparison with conventional, open systems and methods (SERVA, Miltenyi Biotec). Using said closed system, it is possible to carry out a closed and automated isolation method for the stem cells, especially primary MSCs. Manual activities on said closed system can be reduced to a minimum. In the case of the isolation of primary MSCs, a very high initial amount of MSCs is achieved as a result of a particularly efficient tissue digestion, especially when using umbilical cord tissue. The completely closed system thus designed also allows the use or connection of a likewise closed system for the expansion of the cells (e.g., HYPERStack®, Corning). Since any contact by the users with the isolated cells can be avoided owing to the system being closed, the risk of contamination is greatly reduced. Lastly, the device according to the invention, especially when it is realized as a closed system, is particularly advantageous, since it can provide high amounts of young, lowly expanded cells for clinical applications.

Optionally, the device according to the invention can further contain a control unit. Said control unit is optionally disconnectable from the device according to the invention, especially when the device according to the invention is to be disinfected or sterilized, such as autoclaved for example, as a closed system or is to be used as a closed system containing, in part, sterilizable components (isolation chamber, comminution mechanism, etc.) and, in part, components realized as disposable product, such as hoses and bag systems for example, which can be sterile-connected to form a closed system before the start of the isolation of the MSCs.

The control unit can be a process computer or a conventionally available computer system, such as, for example, a laptop or a personal computer. It is also possible for the control unit to be a smartphone or a tablet computer. In this case, the control unit is preferably connected wirelessly (e.g., via WLAN or Bluetooth®) to the device according to the invention. The control unit serves to control and to regulate all the necessary processes in the device according to the invention, or to control the individual components of the device according to the invention. For instance, it is possible by means of the control unit, preferably by means of process software installed on the control unit, to regulate the rotational speed of the rotating knife system for the mechanical dissociation of the fetal tissue. The rotating knife system operates, for example, at a rotational speed within the range from 1000 to 10 000 $min^{-1}$, preferably within the range from 1000 to 9000 $min^{-1}$, 1000 to 8000 $min^{-1}$, 1000 to 7000 $min^{-1}$, 1000 to 6000 $min^{-1}$, 1500 to 5000 $min^{-1}$ or 1500 to 4000 $min^{-1}$, particularly preferably within the range from 2000 to 3000 $min^{-1}$. Using the control unit, it is also possible to control the temperature in the incubation chamber during the tissue disruption. The control unit can also control the pumps present in the device according to the invention. For example, it is possible for time and amount of addition of the tissue-disruption solution from the corresponding reservoir and time and amount of addition of the rinse solution to be regulated by the control unit. The pumps which convey the tissue-disruption suspension after mechanical dissociation and enzymatic digestion into a following density-gradient centrifuge and/or a means for the expansion of the isolated stem cells can, too, be controlled or regulated by means of the control unit.

The fetal tissue which can be processed using the device according to the invention is, for example, selected from umbilical cord tissue, placenta tissue, fetal lung tissue, etc. In a particularly preferred embodiment, the device according to the invention is used to process fetal tissue from umbilical cord. In a further preferred embodiment, the stem cells which can be isolated with the aid of the device according to the invention are mesenchymal stem cells, such as, for example, mesenchymal stem cells which can be isolated from the aforementioned tissues. In a very particularly preferred embodiment, the mesenchymal stem cells are MSCs from umbilical cord tissue.

The isolation of the stem cells from fetal tissues using the device according to the invention can be done in a batch process or in continuous processes. Preferably, the isolation of the stem cells, especially of MSCs, using the device according to the invention is carried out in a batch process, wherein each batch uses an entire umbilical cord as starting product for the isolation of the stem cells. Each product batch (isolated and/or expanded stem cells) then consists of the stem cells, especially primary MSCs, which were isolated from an umbilical cord and had then been optionally expanded.

The invention also relates to the use of the device according to the invention for isolating stem cells from other fetal and/or adult tissues.

The invention further provides a method for isolating stem cells from fetal tissue, which method is adapted specifically to the device according to the invention and, in particular, its realization as a closed system.

In one embodiment, the method according to the invention for isolating stem cells, especially primary MSCs, from fetal tissue comprises the following steps:
  a. mechanical dissociation of the fetal tissue,
  b. enzymatic digestion of the fetal tissue,
  c. optionally density-gradient centrifugation for the removal of impurities, and
  d. optionally expansion of the isolated stem cells, especially the primary MSCs.

The advantage of the method according to the invention is that the mechanical dissociation and the enzymatic digestion can be carried out simultaneously in the incubation chamber of the device according to the invention.

For the enzymatic digestion of the fetal tissue, preference is given to using an enzyme mixture which has already been described above for the device according to the invention.

Preferably, when carrying out the method according to the invention in the incubation chamber of the device according to the invention, the mixture for the enzymatic digestion is stirred and/or heated continuously.

In a further embodiment, the method according to the invention is carried out in an oxygen-depleted atmosphere containing, for example, an oxygen concentration within the range of 2-21%, preferably 2-15% or 2-10%, particularly preferably of 2-5%. As a result, it is possible to avoid oxidative stress for the stem cells, especially primary MSCs, which are to be isolated and which normally reside in hypoxic compartments. As a result, it is possible to distinctly increase the quality of the cell product after performance of the method according to the invention. When using the device according to the invention for isolating specific cells, such as adult lung cells for example, it is advantageous to adjust the oxygen concentration in the atmosphere of the incubation chamber to 21%.

In a further embodiment, the method according to the invention after the expansion of the stem cells further comprises the harvesting of the culture supernatant. The culture supernatant can subsequently be processed and be used as a therapeutic cell-free product.

Using the device according to the invention, it is possible for the thus obtained product (culture supernatant) to be concentrated inline by means of conventional filtration and dialysis techniques. This has the advantage that the device according to the invention and the method according to the invention can be used for the GMP-compliant production of cell-free products as well, for example conditioned, purified cell-culture medium; exosomes, etc.

In a further embodiment, the method according to the invention also encompasses the harvesting of the stem cells, especially the primary MSCs.

In a particularly preferred embodiment, the method according to the invention for isolating stem cells from fetal tissue comprises the steps of
  a. collection of a sample from fetal tissue,
  b. mechanical dissociation of the fetal tissue,
  c. enzymatic digestion of the fetal tissue,
  d. optionally density-gradient centrifugation for the removal of impurities, and
  e. optionally expansion of the isolated stem cells,
  f. optionally inline-concentration of the culture supernatant after the harvesting of the expanded cells.

The invention will be elucidated below on the basis of three figures and one exemplary embodiment.

FIG. 1 shows the device 10 according to the invention as a closed system. The device comprises an incubation chamber 11 with lid 28, a reservoir for the tissue-disruption solution 12 and a reservoir for the rinse solution 13. The reservoirs for the tissue-disruption solution 12 and the rinse solution 13 are both connected to the incubation chamber 11 via hoses 20 and the ports 16 and 17. The tissue-disruption solution can be conveyed from the reservoir 12 into the incubation chamber 11 by means of the peristaltic pump 14. The rinse solution can be filled into the incubation chamber 11 from the reservoir 13 by means of the peristaltic pump 15. The incubation chamber 11 contains a rotating cutting knife 21 for the mechanical dissociation of the fetal tissue. The temperature in the incubation chamber 11 can be regulated by means of an electric heating rod 24 and a temperature sensor 23. Alternatively, the temperature in the incubation chamber can also be regulated by means of a Peltier element provided with a sterilizable or disposable shell. The pH of the tissue-disruption solution in the incubation chamber 11 can be monitored by means of the optional pH probe 22. The incubation chamber 11 additionally has an outlet 18 which is connected via hoses 20 to a HYPERStack® system from Corning for the subsequent adherent cell expansion. After performance of mechanical dissociation and enzymatic digestion, the tissue-disruption suspension can be transferred from the incubation chamber 11 into the HYPERStack® System 25 by means of the peristaltic pump 19. The device 10 can be controlled using a smartphone or tablet PC 29 as control unit. Said control unit can, for example, be connected wirelessly to the device 10.

Figure 2:
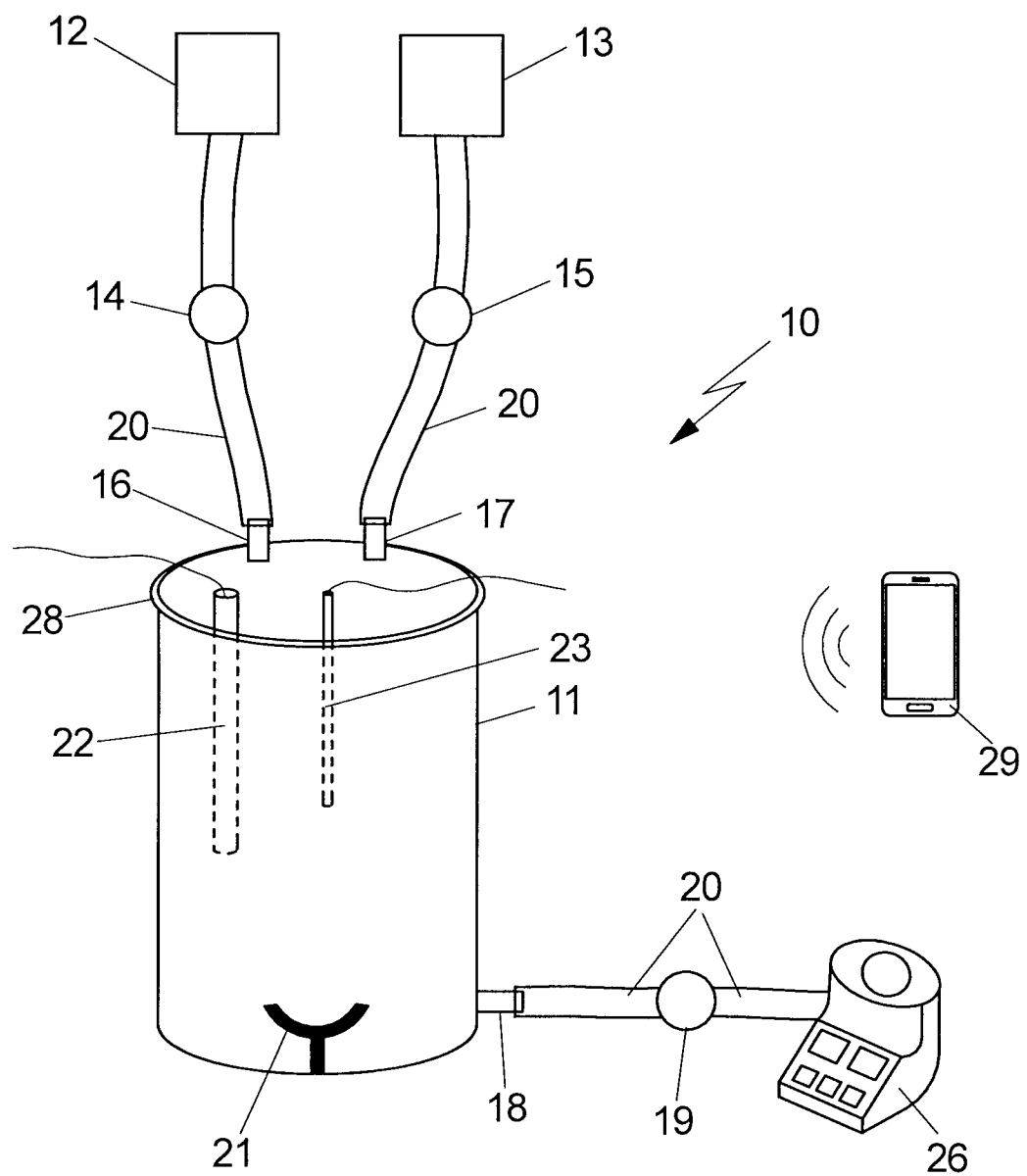

FIG. 2 shows a device according to the invention that is realized as a closed system, as in FIG. 1. In contrast to the embodiment in FIG. 1, the device according to FIG. 2 contains a density-gradient centrifuge 26 instead of the HYPERStack® system 25.

Alternatively, the device according to the invention can also contain a density-gradient centrifuge 26 and a HYPERStack® system 25.

Figure 3:
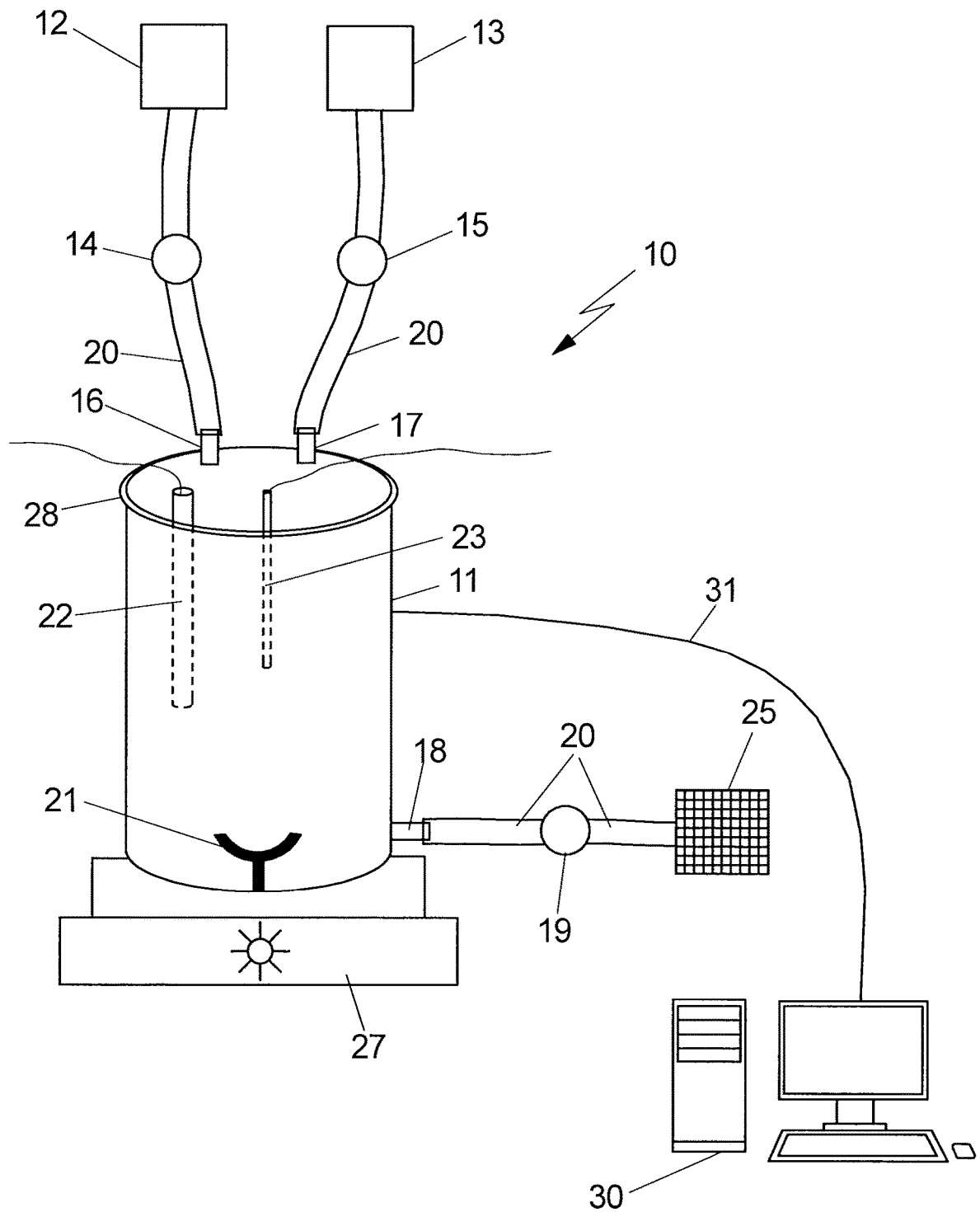

FIG. 3 shows one embodiment of the device according to the invention as a closed system, as shown in FIG. 1. In contrast to FIG. 1, the temperature in the incubation chamber 11 is adjusted by means of a heating plate 27 instead of an electric heating rod 24. Alternatively, the temperature in the incubation chamber can also be regulated by means of a Peltier element provided with a sterilizable or disposable shell.

The device 10 can be controlled using a PC 30 as control unit, with PC 30 and device 10 being, for example, cable-connected via the cable 31.

EXEMPLARY EMBODIMENT: ISOLATION OF A BATCH OF PRIMARY MSCS FROM AN UMBILICAL CORD

A batch of MSCs was obtained from an umbilical cord using the device according to the invention and the method according to the invention. To this end, the umbilical cord was first stored under controlled conditions until the transport to the device 10 according to the invention. The storage was done at a temperature of 4° C. and in a specific medium composed of a citrate-phosphate-dextrose-adenine solution (CPDA1) and PBS (CDPA1/PBS).

The transport to the device 10 according to the invention was likewise done under controlled conditions at a temperature of 4° C. in the medium CPDA1/PBS.

The isolation of the MSCs from the umbilical cord was then carried out in the device 10 according to the invention. To this end, the entire umbilical cord was placed into the incubation tank 11, which was closed with the lid 28. Before the performance of the MSC isolation, the entire device 10 was sterilized. The mechanical disruption of the umbilical cord was done automatically by means of the rotating knife system 21 after closure of the lid 28 in the incubation chamber 11.

This was followed by the enzymatic dissociation using an AoF enzyme mixture which contained recombinant collagenase, hyaluronidase and DNAse of eukaryotic origin. The DNAse was Pulmozyme (Roche Diagnostics). The collagenase used was collagenase NB IV/VI (SERVA Electrophoresis). The tissue-disruption solution (50 ml) additionally contained Dulbecco's modified Eagle medium (DMEM). Also present in the tissue-disruption solution were glucose and HEPES. The tissue-disruption solution was introduced into the incubation chamber from the reservoir 12 via the inlet 16 by means of peristaltic pump 14.

The enzymatic dissociation, which was carried out for 3 h, was followed by a density-gradient separation in a CEPA centrifuge (Carl Padberg, Zentrifugenbau GmbH) 26. To this end, the incubation chamber 11 was first rinsed by introduction of 50 ml of rinse solution (Dulbecco's phosphate buffered saline (PBS)) from the reservoir 13 by means of the peristaltic pump 15. Via the outlet 18 and by means of the peristaltic pump 19, the tissue-disruption solution was then transferred into the density-gradient centrifuge 26 via the hoses 20. The density-gradient centrifugation was carried out using Ficol® tubes. Performance of the density-gradient separation was followed by the transfer and seeding of the primary culture into a closed cell-culture system from HYPERStack® (Corning) 25. The yield before the expansion of the target cells was approx. $1 \times 10^6$ cells per umbilical cord. The subsequent cell expansion, necessary media change and the cell harvesting was done with AoF reagents in the closed system of the device 10. Altogether only two passages were required in order to reach a target cell count of $1 \times 10^9$ cells. The cell harvesting was followed by the cryopreservation. A sterility test, a FACS analysis and a potency assay were carried out for the quality control.

The target cells of the thus worked-up MSC batch bear the surface markers CD73, CD90 and CD105, but do not bear the surface markers CD14, CD34 and CD45. With the purification of a batch of MSCs from an umbilical cord that was carried out by means of the device 10 according to the invention, it was possible to achieve a purity of greater than 95% of the target cells bearing the surface markers CD73, CD90 and CD105. Less than 2% of the purified cells bore the unwanted markers CD14, CD34 and CD45.

The table below illustrates the process for producing a batch of MSCs from umbilical cord tissue using the device according to the invention.

|  | Invention | Prior art |
| --- | --- | --- |
| Obtaining the starting material (umbilical cord) | Controlled storage until transport (specif. temperature and specif. medium) | Uncontrolled storage/not specified |
|  | Controlled transport for work-up (specif. temperature and specif. medium) | Uncontrolled transport/not specified |

-continued

|  | Invention | Prior art |
|---|---|---|
| Isolation of the MSC from the umbilical cord | Automatic, mechanical dissociation Enzymatic dissociation with specif. AoF enzyme cocktail Density-gradient separation with specif. separation medium Seeding of primary culture in closed cell-culture system | Manual processing by e.g. scratching of the surface or manual dissociation — Plating out of the tissue pieces in Petri dishes (open system) |
| Expansion | Cell expansion, medium change and cell harvesting with AoF reagents in completely closed system | Cell expansion, medium change and cell harvesting, in some cases with calf serum and trypsin, in open system |
|  | Low number of passages necessary (<P3) for reaching target cell count of $1 \times 10^9$ cells | Distinctly more passages necessary (>P5) for reaching target cell count of $1 \times 10^9$ cells |
| Cryopreservation | Cryopreservation | Cryopreservation |
| Quality control | Sterility test FACS analysis with extended panel Potency assay | Sterility test FACS analysis with standard panel — |
| Yield | Approx. $1 \times 10^6$ cells/umbilical cord | Approx. $1 \times 10^5$ cells/umbilical cord |
| Purity (CD73+, CD90+, CD105+) | >95% | >80% |
| Purity (CD14−, CD34−, CD45−) | <2% | <10% |

LIST OF REFERENCE SIGNS

10 Device for isolating stem cells from fetal tissues
11 Incubation chamber
12 Reservoir for tissue-disruption solution
13 Reservoir for rinse solution
14 Peristaltic pump for pumping the tissue-disruption solution
15 Peristaltic pump for pumping the rinse solution
16 Port for the tissue-disruption solution
17 Port for the rinse solution
18 Outlet
19 Peristaltic pump for pumping the tissue-disruption suspension
20 Hoses
21 Rotating knife system
22 pH probe
23 Temperature sensor
24 Electric heating rod or Peltier element
25 HYPERStack® system
26 Density-gradient centrifuge
27 Electric heating plate
28 Lid
29 Smartphone, tablet PC
30 PC
31 Cable

REFERENCES

T. R. J. Heathman et al., "The translation of cell-based therapies: clinical landscape and manufacturing challenges.", Regen Med, vol. 10, no. 1, pp. 49-64, 2015;

M. Mendicino et al., "MSC-based product characterization for clinical trials: an FDA perspective.", Cell Stem Cell, vol. 14, no. 2, pp. 141-145, February 2014;

P. Wuchter et al., "Standardization of good manufacturing practice-compliant production of bone marrow-derived human mesenchymal stromal cells for immunotherapeutic applications.", Cytotherapy, vol. 17, no. 2, pp. 128-139, February 2015;

R. Hass et al., "Different populations and sources of human mesenchymal stem cells (MSC): A comparison of adult and neonatal tissue-derived MSC.", Cell Commun Signal, vol. 9, p. 12, May 2011;

I. Majore et al., "Growth and differentiation properties of mesenchymal stromal cell populations derived from whole human umbilical cord.", Stem Cell Rev, vol. 7, no. 1, pp. 17-31, March 2011;

R. Sarugaser et al., "Human umbilical cord perivascular (HUCPV) cells: a source of mesenchymal progenitors.", Stem Cells, vol. 23, no. 2, pp. 202-229, February 2005;

N. Tsagias et al., "Isolation of mesenchymal stem cells using the total length of umbilical cord for transplantation purposes.", Transfus Med, vol. 21, no. 4, pp. 253-261, August 2011;

M. M. Lalu et al., "Safety of cell therapy with mesenchymal stromal cells (SafeCell): a systematic review and meta-analysis of clinical trials.", PLoS One, vol. 7, no. 10, pp. e47559, October 2012;

P. Monsarrat et al., "An Innovative, Comprehensive Mapping and Multiscale Analysis of Registered Trials for Stem Cell-Based Regenerative Medicine.", Stem Cells Transl Med, vol. 5, no. 6, pp. 826-835, June 2016;

T. van Haaften et al., "Airway delivery of mesenchymal stem cells prevents arrested alveolar growth in neonatal lung injury in rats.", Am J Respir Crit Care Med, vol. 180, no. 11, pp. 1131-1142, December 2009;

Y. S. Chang et al., "Mesenchymal stem cells for bronchopulmonary dysplasia: phase 1 dose-escalation clinical trial.", J Pediatr, vol. 164, no. 5, pp. 966-972, May 2014;

M. A. Möbius, B. Thébaud, "Cell Therapy for Bronchopulmonary Dysplasia: Promises and Perils.", Paediatr. Respir. Rev. in press (2016);

G. Yannarelli et al., "Human umbilical cord perivascular cells exhibit enhanced cardiomyocyte reprogramming and cardiac function after experimental acute myocardial infarction.", Cell Transplant, vol. 22, no. 9, pp. 1651-1666, 2013.

The invention claimed is:

1. A device for isolating stem cells from a fetal tissue, comprising:
   an incubation chamber,
   at least one pump,
   at least one reservoir for a tissue-disruption solution, which is connectable to the incubation chamber,
   at least one reservoir for a rinse solution, which is connectable to the incubation chamber,
   optionally a control unit,
   a means for the removal of impurities in a density gradient, and
   optionally a means for the expansion of isolated stem cells,
   wherein the incubation chamber comprises a lower region having a rotating knife system for comminution of fetal tissues, wherein the rotating knife system is positioned and configured to stir the tissue-disruption solution with the fetal tissues in the lower region of the incubation chamber,
   wherein the accessibility of the fetal tissues for the tissue-disruption solution is ensured at all times, and
   wherein the device is a closed system.

2. The device as claimed in claim 1, wherein the incubation chamber is a heatable or a nonheatable tank.

3. The device as claimed in claim 1, wherein the means for the removal of impurities in a density gradient is a centrifuge.

4. The device as claimed in claim 1, wherein the incubation chamber comprises openings/ports for lines and hoses.

5. The device as claimed in claim 4, wherein the tissue-disruption solution and/or the rinse solution can be added to the incubation chamber via the openings/ports.

6. The device as claimed in claim 5, wherein the reservoir for the tissue-disruption solution and/or the reservoir for the rinse solution are connected to the incubation tank by means of hoses via the openings/ports.

7. The device as claimed in claim 1, wherein the incubation chamber comprises at least one outlet.

8. The device as claimed in claim 7, wherein a tissue-disruption solution can be transferred into other tanks via the at least one outlet.

9. The device as claimed in claim 7, wherein the at least one outlet is connected to the means for the expansion of the isolated cells by means of hoses.

10. The device as claimed in claim 1, wherein the device is the closed system, which is sterilizable.

11. The device as claimed in claim 1, wherein the at least one pump includes a peristaltic pump.

12. The device as claimed in claim 1, wherein the device further contains a means for the inline-concentration of a culture supernatant after harvesting of expanded cells.

13. The device as claimed in claim 1, wherein the fetal tissue is selected from the group consisting of umbilical cord tissue, placenta tissue, tissue from the fetal membranes, and fetal lung tissue.

14. The device as claimed in claim 1, wherein the fetal tissue is at least one entire umbilical cord.

15. The device as claimed in claim 1, wherein the stem cells are mesenchymal stem cells.

16. The device as claimed in claim 1, wherein cell-free products are obtained.

17. The device as claimed in claim 1, wherein the at least one reservoir for the tissue-disruption solution contains the tissue-disruption solution, wherein the tissue-disruption solution contains a mixture of enzymes hyaluronidase and neutral protease and/or collagenase and/or DNAse; or a mixture of the enzymes DNAse and hyaluronidase and/or neutral protease and/or collagenase.

18. A system comprising:
   the device of claim 1; and
   the tissue-disruption solution, which contains a mixture of enzymes hyaluronidase and neutral protease and/or collagenase and/or DNAse; or a mixture of the enzymes DNAse and hyaluronidase and/or neutral protease and/or collagenase.

* * * * *